(12) United States Patent
Bhirud et al.

(10) Patent No.: US 9,840,456 B2
(45) Date of Patent: Dec. 12, 2017

(54) PROCESS FOR PREPARATION OF DIMETHYL FUMARATE

(71) Applicant: Glenmark Pharmaceuticals Limited, Mumbai (IN)

(72) Inventors: Shekhar Bhaskar Bhirud, Mumbai (IN); Kumar Hari Bhushan, Gurgaon (IN); H M Veerabhadra Swamy, Bangalore (IN); Dilipkumar Jibhau Patil, Nasik (IN); Avikumar Digambar Dabe, Nasik (IN)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 0 days.

(21) Appl. No.: 15/025,056

(22) PCT Filed: Sep. 22, 2014

(86) PCT No.: PCT/IB2014/064726
§ 371 (c)(1),
(2) Date: Mar. 25, 2016

(87) PCT Pub. No.: WO2015/044853
PCT Pub. Date: Apr. 2, 2015

(65) Prior Publication Data
US 2016/0237021 A1    Aug. 18, 2016

(30) Foreign Application Priority Data

Sep. 25, 2013 (IN) .......................... 3070/MUM/2013

(51) Int. Cl.
*C07C 67/48* (2006.01)
*C07C 69/60* (2006.01)
*C07C 67/08* (2006.01)
*C07C 67/60* (2006.01)

(52) U.S. Cl.
CPC .............. *C07C 69/60* (2013.01); *C07C 67/08* (2013.01); *C07C 67/60* (2013.01)

(58) Field of Classification Search
CPC .......... C07C 67/08; C07C 67/60; C07C 69/60
See application file for complete search history.

(56) References Cited

U.S. PATENT DOCUMENTS

| 9,422,226 B2 * | 8/2016 | Guzowski | ............... C07C 67/08 |
| 2012/0034303 A1 * | 2/2012 | Nilsson | ................ A61K 9/2054 424/472 |
| 2016/0206587 A1 * | 7/2016 | Galetzka | .............. A61K 9/0053 |

FOREIGN PATENT DOCUMENTS

| CN | 102766050 A | 11/2012 |
| WO | 2012170923 A1 | 12/2012 |
| WO | WO2012/170923 | * 12/2012 |

OTHER PUBLICATIONS

Beattie et al, A European Journal, 10(30), 8972-74, 2010(abstract only).*
Beattie et al. (Supporting Information, Chemistry a European Journal, 8 pages, published 2010.*
J.K. Beattie et al., "The Mechanism of On-Water Catalysis," Chemistry A European Journal, Aug. 9, 2010, pp. 8972-8974, vol. 16, No. 30.
J.K. Beattie et al., "The Mechanism of On-Water Catalysis: Supporting Information" Chemistry A European Journal, 2010, 8 pages.

* cited by examiner

*Primary Examiner* — Yevegeny Valenrod
*Assistant Examiner* — Blaine G Doletski
(74) *Attorney, Agent, or Firm* — Ryan, Mason & Lewis, LLP

(57) ABSTRACT

The present invention relates to a process for the preparation of dimethyl fumarate, a compound of formula I, in a purity of at least 99.0% as determined by HPLC, containing less than 400 ppm of an anion of a mineral acid and less than 5 ppm of dimethyl maleate.

8 Claims, 1 Drawing Sheet

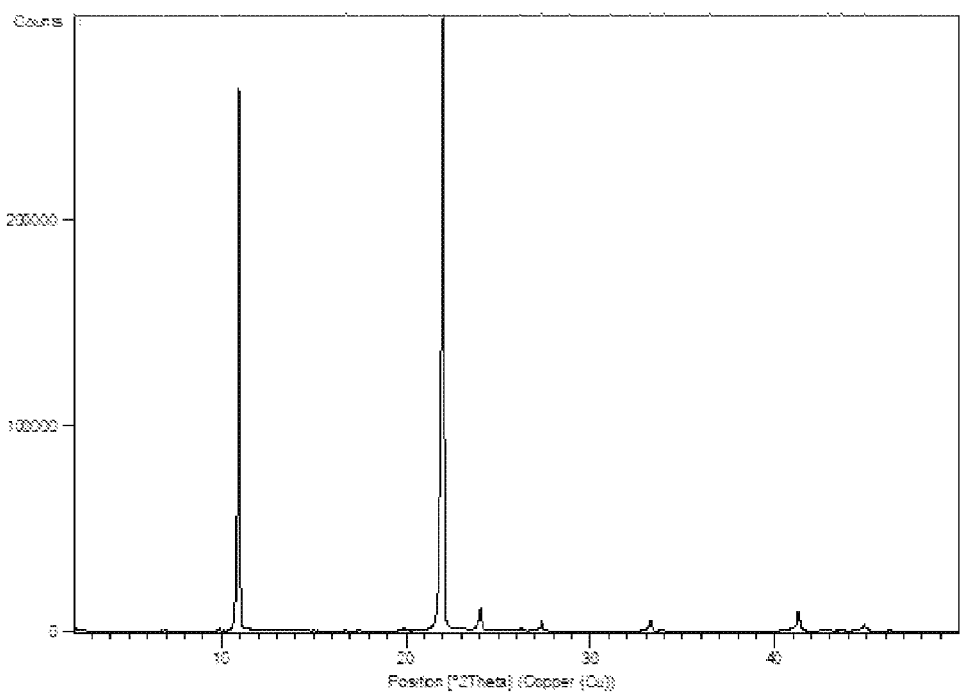

PROCESS FOR PREPARATION OF DIMETHYL FUMARATE

PRIORITY

This application claims priority under 35 U.S.C. §371 to International Application No. PCT/IB2014/064726, filed Sep. 22, 2014 which claims the benefit of Indian Provisional Application No. 3070/MUM/2013, filed Sep. 22, 2013, the contents of which are incorporated by reference herein.

FIELD OF THE INVENTION

The present invention relates to a process for the preparation of dimethyl fumarate.

BACKGROUND OF THE INVENTION

Dimethyl fumarate is represented by the structure of formula I.

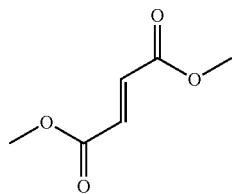

Dimethyl fumarate is indicated for the treatment of patients with relapsing forms of multiple sclerosis. Dimethyl fumarate is marketed under the brand name TECFIDERA® in the United States.

Processes for the preparation of dimethyl fumarate known in the art show presence of impurities such as dimethyl sulfate, monomethyl fumarate, dimethyl maleate in dimethyl fumarate. Use of acid such as sulfuric acid as a catalyst in esterification reaction is also known to pose several problems such as corrosion of reaction vessels, catalyst recovery and waste disposal.

Impurities in dimethyl fumarate or any active pharmaceutical ingredient (API) are undesirable and, in extreme cases, might even be harmful to a patient being treated with a dosage form containing the API.

It is also known in the art that impurities in an API may arise from degradation of the API itself, which is related to the stability of the pure API during storage, and the manufacturing process, including the chemical synthesis. Process impurities include unreacted starting materials, chemical derivatives of impurities contained in starting material, synthetic by-products, and degradation products.

Impurities introduced during commercial manufacturing processes must be limited to very small amounts, and are preferably substantially absent.

Thus there is a need in the art for improved processes for preparing pure dimethyl fumarate, which are more industrially applicable.

The present invention provides commercially viable simple scalable process for the preparation of dimethyl fumarate free of genotoxic impurities.

SUMMARY OF THE INVENTION

The present invention provides a process for the preparation of dimethyl fumarate, a compound of formula I,

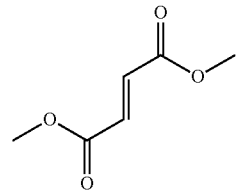

in a purity of at least 99.0% as determined by HPLC, containing less than 400 ppm of an anion of a mineral acid and less than 5 ppm of dimethyl maleate, the process comprising:
(a) reacting fumaric acid with an acyl halide in methanol to obtain dimethyl fumarate, a compound of formula I;
(b) subjecting dimethyl fumarate, the compound of formula I to treatment with a base; and
(c) isolating dimethyl fumarate, the compound of formula I in a purity of at least 99.0% as determined by HPLC, containing less than 400 ppm of an anion of a mineral acid and less than 5 ppm of dimethyl maleate.

In another embodiment, the present invention provides dimethyl fumarate, a compound of formula I, containing less than 400 ppm of an anion of a mineral acid.

In another embodiment, the present invention provides dimethyl fumarate, a compound of formula I, containing less than 400 ppm of an anion of a mineral acid and free of dimethyl sulfate.

In another embodiment, the present invention provides dimethyl fumarate, a compound of formula I, containing less than 400 ppm of an anion of a mineral acid, free of dimethyl sulfate and having monomethyl fumarate content of less than 0.15%.

In another embodiment, the present invention provides dimethyl fumarate, a compound of formula I, containing less than 400 ppm of an anion of a mineral acid, free of dimethyl sulfate and having monomethyl fumarate content of less than 0.15% and dimethyl maleate content of less than 5 ppm.

In another embodiment, the present invention provides dimethyl fumarate, a compound of formula I, containing less than 5 ppm of dimethyl maleate.

BRIEF DESCRIPTION OF THE ACCOMPANYING FIGURE

The FIGURE is an XRD pattern of dimethyl fumarate according to example 6.

DETAILED DESCRIPTION OF THE INVENTION

The present invention provides a process for the preparation of dimethyl fumarate, a compound of formula I,

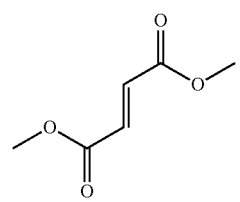

in a purity of at least 99.0% as determined by HPLC, containing less than 400 ppm of an anion of a mineral acid and less than 5 ppm of dimethyl maleate, the process comprising:
(a) reacting fumaric acid with an acyl halide in methanol to obtain dimethyl fumarate, a compound of formula I;
(b) subjecting dimethyl fumarate, the compound of formula I to treatment with a base; and
(c) isolating dimethyl fumarate, the compound of formula I in a purity of at least 99.0% as determined by HPLC, containing less than 400 ppm of an anion of a mineral acid and less than 5 ppm of dimethyl maleate.

In the present application, the term "room temperature" means a temperature of about 25° C. to about 30° C. The term "anion of a mineral acid" includes group consisting of chloride, bromide, iodide, fluoride, sulphate, nitrate and phosphate. The term "acyl" includes groups such as acetyl, optionally substituted benzoyl, pivaloyl. The term "optionally substituted benzoyl" means benzoyl which is optionally substituted with halo or nitro group wherein halo includes Cl, Br, I. The term "halide" includes group consisting of chloride, bromide, iodide.

In (a) of the process for the preparation of dimethyl fumarate, fumaric acid is reacted with an acyl halide in methanol to obtain dimethyl fumarate, the compound of formula I.

The acyl halide that may be utilized for this step includes, but is not limited to acetyl chloride, acetyl bromide, acetyl fluoride.

The reaction may be carried out at a temperature in the range of about 25° C. to about the reflux temperature of the solvent. Preferably the reaction is carried out at a temperature of about 40° C. to about 65° C.

The reaction is carried out for a period of about 1 hour to about 15 hours. Preferably the reaction is carried out for a period of about 2 hours to about 6 hours.

The molar equivalent of acyl halide employed is from about 0.5 times the molar amount to about 3 times the molar amount with respect to fumaric acid. Preferably acyl halide used is in the range from about an equimolar amount to about 2 times the molar amount of fumaric acid.

In one embodiment, the molar equivalent of acyl halide employed is ≥0.5% times the molar amount with respect to fumaric acid.

In one embodiment, fumaric acid is reacted with acetyl chloride in methanol to obtain dimethyl fumarate.

In (b) of the above process, dimethyl fumarate, the compound of formula I is subjected to treatment with a base.

Treatment of dimethyl fumarate with a base includes either dissolving dimethyl fumarate in a suitable solvent followed by washing with a base, or slurrying dimethyl fumarate with a base, or directly treating the reaction mixture containing dimethyl fumarate with a base.

The base that may be utilized for this step includes, but is not limited to alkali metal hydroxides such as lithium hydroxide, sodium hydroxide, potassium hydroxide; alkaline earth metal hydroxides; alkali metal carbonates such as sodium carbonate, potassium carbonate, caesium carbonate; alkaline earth metal carbonates; alkali metal bicarbonates such as sodium bicarbonate. Preferably the base selected is sodium bicarbonate.

In one embodiment, the reaction mixture containing dimethyl fumarate is treated with a base.

In one embodiment, dimethyl fumarate is isolated from the reaction mixture and then treated with a base.

In one embodiment, dimethyl fumarate, the compound of formula I is isolated from the reaction mixture and then slurred in aqueous base solution.

In one embodiment, dimethyl fumarate, the compound of formula I is isolated from the reaction mixture and then slurred in aqueous sodium bicarbonate solution.

Advantageously the treatment of compound of formula I with base leads to dimethyl fumarate free of genotoxic impurity methyl chloride and having less than 400 ppm of an anion of a mineral acid.

The content of impurities in dimethyl fumarate such as an anion of a mineral acid, fumaric acid, dimethyl sulfate, monomethyl fumarate, dimethyl maleate is monitored by analytical techniques described herein.

In (c) of the above process, dimethyl fumarate, the compound of formula I is isolated with a purity of at least 99.0% as determined by HPLC, containing less than 400 ppm of an anion of a mineral acid and less than 5 ppm of dimethyl maleate.

In one embodiment, the isolation of the compound of formula I includes crystallization in a solvent.

The solvent that may be utilized for this step includes, but is not limited to alcohols such as methanol, ethanol, 1-propanol, 2-propanol, 1-butanol, 2-butanol, 1-pentanol, 1-octanol and the like; esters such as methyl acetate, ethyl acetate, n-propyl acetate, and tert-butyl acetate and the like; ketones such as acetone, ethyl methyl ketone and methyl isobutyl ketone and the like; ethers such as dimethyl ether, diethyl ether, diisopropyl ether, tert-butyl methyl ether, tetrahydrofuran, dioxane and the like; haloalkanes such as dichloromethane, chloroform and the like; acetonitrile; dimethyl sulfoxide; dimethyl formamide; dimethyl acetamide; water or mixtures thereof. Preferably the solvent selected is methanol.

In one embodiment, the isolation of the compound of formula I includes crystallization in methanol.

Removal of solvent may be accomplished by substantially complete evaporation of the solvent or concentrating the solution, cooling the solution if required and filtering the obtained solid.

The solid material obtained above may be further dried. Drying may be suitably carried out by any method, known in the art, including but not limited to, using a tray drier, vacuum oven, air oven, fluidized bed drier, spin flash drier, flash drier, and the like. The drying may be carried out under reduced pressures and at elevated temperatures. The temperature may range from about ambient temperature to about 100° C., for a time period that produces the desired result.

In one embodiment, the drying may be carried out at temperature range of 25-30° C., for a period of about 6 hours followed by drying at temperature range of 45-50° C.

In one embodiment, the isolation of the compound of formula I is carried out without use of column chromatography purification.

In one embodiment, the isolation of the compound of formula I in a purity of at least 99% is carried out directly from the reaction mixture without use of column chromatography purification.

In one embodiment, the present invention provides a process for the preparation of dimethyl fumarate, a compound of formula I, in a purity of at least 99.0% as determined by HPLC, containing less than 400 ppm of an anion of a mineral acid and less than 5 ppm of dimethyl maleate, the process comprising:
(a) reacting fumaric acid with an acyl halide in methanol to obtain dimethyl fumarate, a compound of formula I;

(b) subjecting dimethyl fumarate, the compound of formula I to treatment with a base; and (c) isolating dimethyl fumarate, the compound of formula I in a purity of at least 99.0% as determined by HPLC, containing less than 400 ppm of an anion of a mineral acid and less than 5 ppm of dimethyl maleate without use of column chromatography purification.

In one embodiment, the present invention provides a process for the preparation of dimethyl fumarate, a compound of formula I, in a purity of at least 99.0% as determined by HPLC, containing less than 400 ppm of chloride ion and less than 5 ppm of dimethyl maleate, the process comprising:

(a) reacting fumaric acid with an acyl halide in methanol to obtain dimethyl fumarate, a compound of formula I;

(b) subjecting dimethyl fumarate, the compound of formula I to treatment with a base; and (c) isolating dimethyl fumarate, the compound of formula I in a purity of at least 99.0% as determined by HPLC, containing less than 400 ppm of chloride ion and less than 5 ppm of dimethyl maleate In one preferred embodiment, the present invention provides a process for the preparation of dimethyl fumarate, a compound of formula I, in a purity of at least 99.0% as determined by HPLC, containing less than 100 ppm of chloride ion and less than 3.5 ppm of dimethyl maleate, the process comprising:

(a) reacting fumaric acid with acetyl chloride in about equimolar amounts in methanol to obtain dimethyl fumarate, a compound of formula I;

(b) subjecting dimethyl fumarate, the compound of formula I to treatment with alkali metal bicarbonate; and (c) isolating dimethyl fumarate, the compound of formula I in a purity of at least 99.0% as determined by HPLC, containing less than 100 ppm of chloride ion and less than 3.5 ppm of dimethyl maleate The compound of formula I prepared by the process of the present invention has a purity of at least about 99.0%. Preferably the total purity is at least about 99.5%, more preferably the total purity is at least about 99.9%, as measured by high performance liquid chromatography.

The compound of formula I prepared by the process of the present invention has fumaric acid content of less than 0.2%, preferably less than 0.1%, more preferably less than 0.05%, as measured by high performance liquid chromatography.

Fumaric acid is a known compound and can be prepared by processes known in the art. Fumaric acid can be prepared by isomerization of maleic acid, by heating malic acid, by oxidation of furfural, by reduction of tartaric acid with phosphorus and iodine.

In one embodiment, maleic anhydride was heated in water to give maleic acid which was converted to fumaric acid in presence of inversion agent such as thiourea.

In one embodiment, fumaric acid obtained is slurried in water and the slurry obtained is heated at 85-90° C. for about 30 minutes, followed by cooling the slurry at 25-30° C. and maintaining at 25-30° C. and isolating the fumaric acid.

In one embodiment, fumaric acid obtained has maleic acid content less than 0.15% w/w as determined by HPLC.

In one embodiment, the present invention provides fumaric acid wherein maleic acid is absent.

The present invention provides dimethyl fumarate, obtained by the above process, having chemical purity, as described, analyzed by using high performance liquid chromatography (HPLC) with the conditions described below:

Reagents, Solvents and Standards:
Water (Milli Q or equivalent)
Perchloric acid 70% (AR Grade)
Acetonitrile (HPLC Grade)
Chromatographic Conditions:
Apparatus: A High Performance Liquid Chromatograph equipped with quaternary gradient pumps, variable wavelength UV detector attached with data recorder and integrator software.
Column: GL Science, Inertsil ODS 3V, 250×4.6 mm, 5µ
Column temperature: 30° C.
Sample cooler temperature: 15° C.
Mobile Phase:
Mobile phase A=Buffer
Buffer: 0.5 mL of Perchloric acid dissolve in 1000 mL of water. (0.05% Perchloric acid in water)
Mobile phase B=Acetonitrile

| Time (min.) | % Mobile Phase A | % Mobile Phase B |
|---|---|---|
| 0.01 | 90 | 10 |
| 03 | 90 | 10 |
| 30 | 50 | 50 |
| 40 | 50 | 50 |
| 43 | 90 | 10 |
| 50 | 90 | 10 |

Diluent: Acetonitrile: Water (20:80, v/v)
Flow Rate: 1.0 mL/minute
Detection: UV 210 nm
Injection Volume: 20 µL
The retention time of dimethyl fumarate is about 20.0 minutes under these conditions. Relative retention time for fumaric acid is about 0.23 and for monomethyl fumarate is about 0.57 with respect to dimethyl fumarate under these conditions.

The present invention provides dimethyl fumarate, obtained by the above process, wherein the amount of an anion of a mineral acid is determined by analytical techniques, for example, chloride ion content can be monitored by ion chromatography, potentiometric titration with silver nitrate, turbidimetric method; sulphate ion content can monitored by ion chromatography, turbidimetric method.

The present invention provides dimethyl fumarate, obtained by the above process, wherein the chloride ion content was determined by USP method as described below:
Preparation of Standard Solution:
Take 0.2 mL of 0.02N hydrochloride acid solution in 30-40 mL of water and mix. Filter this solution through 0.45µ Nylon filter. Add 1 mL each of nitric acid and 0.1N silver nitrate TS and sufficient water to make 50 mL. Mix and allow stand for 5 minutes protected from direct sunlight.
Preparation of Test Solution:
Take 0.35 g sample in suitable test tube. Add 30-40 mL of water and sonicate for 3-4 minutes and filter through 0.45µ Nylon filter. Add 1 mL each nitric acid and 0.1N silver nitrate TS and sufficient water to make 50 mL. Mix and allow stand for 5 minutes protected from direct sunlight. Then compare the turbidity of test and standard solution.

The present invention provides dimethyl fumarate, obtained by the above process, having dimethyl maleate content, as described, analyzed by using high performance liquid chromatography (HPLC) with the conditions described below:
Reagents, Solvents and Standards:
Water (Milli Q or equivalent)
Potassium dihydrogen phosphate (AR Grade)
Acetonitrile (HPLC Grade)
o-phosphoric acid (AR Grade)

Chromatographic Conditions:
Apparatus: A High Performance Liquid Chromatograph equipped with quaternary gradient pumps, variable wavelength UV detector attached with data recorder and integrator software.
Column: GL-Science, Inertsil ODS 3V, 250×4.6 mm, 5μ
Column temperature: 30° C.
Sample cooler temperature: 15° C.
Mobile Phase:
Mobile Phase A=Buffer
Buffer: 0.01M Potassium dihydrogen phosphate. Adjust pH 4.0 with o-phosphoric acid.
Mobile Phase B=Acetonitrile

| Time (min.) | % Mobile Phase A | % Mobile Phase B |
|---|---|---|
| 0.01 | 80 | 20 |
| 03 | 80 | 20 |
| 30 | 50 | 50 |
| 32 | 80 | 20 |
| 40 | 80 | 20 |

Diluent: Acetonitrile:Water (40:60, v/v)
Flow Rate: 1.0 mL/minute
Detection: UV 210 nm
Injection Volume: 50 μL
The retention time of dimethyl maleate is about 10.0 minutes under these conditions.

The present invention provides dimethyl fumarate, a compound of formula I, containing less than 400 ppm of an anion of a mineral acid.

In one embodiment, the present invention provides dimethyl fumarate, a compound of formula I, containing less than 400 ppm of chloride ion.

In one preferred embodiment, the present invention provides dimethyl fumarate, a compound of formula I, containing less than 100 ppm of chloride ion.

The present invention provides dimethyl fumarate, a compound of formula I, containing less than 400 ppm of an anion of a mineral acid and free of dimethyl sulfate.

In one embodiment, the present invention provides dimethyl fumarate, a compound of formula I, containing less than 400 ppm of chloride ion and free of dimethyl sulfate.

In one preferred embodiment, the present invention provides dimethyl fumarate, a compound of formula I, containing less than 100 ppm of chloride ion and free of dimethyl sulfate.

The present invention provides dimethyl fumarate, obtained by the above process, having dimethyl sulphate content, as described, determined by residual solvent analysis using gas chromatography (GC) with the conditions described below:
Chromatographic Parameters:
Instrument: Gas chromatograph equipped with FID detector and autosampler.
Column: DB-1, 30 m×0.32 mm, 1.0 μm
Column Temperature: 40° C. (hold for 2 minutes) to 240° C. @20° C./minute, hold at 240° C. for 20 minutes
Injector/detector: 150° C./270° C.
Carrier gas: Nitrogen
Linear velocity: 30 cm/sec
Split Ratio: (2:1)
Injection Volume: 5.0 μL
Diluent: Dichloromethane (Merck, HPLC grade)

The present invention provides dimethyl fumarate, a compound of formula I, containing less than 400 ppm of an anion of a mineral acid, free of dimethyl sulfate and having monomethyl fumarate content of less than 0.15%.

In one embodiment, the present invention provides dimethyl fumarate, a compound of formula I, having monomethyl fumarate content of less than 0.15% preferably less than 0.1%, more preferably less than 0.05%.

In one embodiment, the present invention provides dimethyl fumarate, a compound of formula I, containing less than 400 ppm of chloride ion, free of dimethyl sulfate and having monomethyl fumarate content of less than 0.15%.

In one preferred embodiment, the present invention provides dimethyl fumarate, a compound of formula I, containing less than 100 ppm of chloride ion, free of dimethyl sulfate and having monomethyl fumarate content of less than 0.05%.

The present invention provides dimethyl fumarate, obtained by the above process, having monomethyl fumarate content, as described, analyzed by HPLC with the conditions as described supra.

The present invention provides dimethyl fumarate, a compound of formula I, containing less than 400 ppm of an anion of a mineral acid, free of dimethyl sulfate and having monomethyl fumarate content of less than 0.15% and dimethyl maleate content of less than 5 ppm.

In one embodiment, the present invention provides dimethyl fumarate, a compound of formula I, having dimethyl maleate content of less than 5 ppm, preferably less than 3.5 ppm.

In one embodiment, the present invention provides dimethyl fumarate, a compound of formula I, containing less than 400 ppm of chloride ion, free of dimethyl sulfate and having monomethyl fumarate content of less than 0.15% and dimethyl maleate content of less than 5 ppm.

In one preferred embodiment, the present invention provides dimethyl fumarate, a compound of formula I, containing less than 100 ppm of chloride ion, free of dimethyl sulfate and having monomethyl fumarate content of less than 0.05% and dimethyl maleate content of less than 3.5 ppm.

The present invention provides dimethyl fumarate, a compound of formula I, containing less than 5 ppm of dimethyl maleate.

In one embodiment, the present invention provides dimethyl fumarate, a compound of formula I, containing less than 3.5 ppm of dimethyl maleate.

The X-Ray powder diffraction of dimethyl fumarate can be measured by an X-ray powder diffractometer equipped with a Cu-anode ($\lambda$=1.54 Angstrom), X-ray source operated at 45 kV, 40 mA and a Ni filter is used to strip K-beta radiation. Two-theta calibration is performed using an NIST SRM 640c Si standard. The sample was analyzed using the following instrument parameters: measuring range=2-50° 2θ; step width=0.017°; and measuring time per step=5 sec.

The D10, D50, and D90 values are useful ways for indicating a particle size distribution. D90 is a size value where at least 90 percent of the particles have a size smaller than the stated value. Likewise D10 refers to 10 percent of the particles having a size smaller than the stated value. D50 refers to at least 50 percent of the particles having a size smaller than the stated value and D[4,3] value refers to a mean particle size. Methods for determining D10, D50, D90 and D [4,3] include those using laser light diffraction with equipment sold by Malvern Instruments ltd.

The particle size distribution of dimethyl fumarate was determined by laser diffraction on Malvern Mastersizer 2000.

In one embodiment, the present invention provides coarser particles of dimethyl fumarate having D90 of at least 400 μm.

In one embodiment, the present invention provides dimethyl fumarate wherein D90 is between 400-600 μm.

The examples that follow are provided to enable one skilled in the art to practice the invention and are merely illustrative of the invention. The examples should not be read as limiting the scope of the invention as defined in the features and advantages.

EXAMPLES

Example 1 Preparation of Fumaric Acid

A suspension of maleic anhydride (250 g) in water (375 mL) was stirred at about room temperature for about 15 min. The reaction mixture was heated to about 45° C. to about 50° C. and was maintained at about the same temperature for about 2 h. Thiourea (7.75 g) was then added to the clear solution at about 45° C. to about 50° C. The reaction mixture was stirred at about the same temperature for about 1 h. The reaction mixture was then cooled to about 10° C. to about 15° C. and maintained at about the same temperature for about 1 h. The solid obtained was filtered and washed with water, dried at about 55° C. to about 60° C. under vacuum for about 12 h. The quality of the product complies as per USP specification. Yield: 290 g

Example 2 Preparation of Dimethyl Fumarate

To a suspension of fumaric acid (500 g) in methanol (2500 mL) was added acetyl chloride (337 g) at controlled temperature (at about below 45° C.) over a period of about 30 min. The reaction mixture was maintained at about 50° C. to about 60° C. for about 5 h. The reaction mixture was then cooled to about 15° C. to about 20° C. and was maintained at about the same temperature for about 1 h. The solid obtained was filtered and washed with methanol. The wet solid was slurred in 2% aqueous sodium bicarbonate solution, filtered and dried at about 25° C. for about 6 h and further dried at about 40° C. to about 45° C. for about 12 h. Yield: 550 g The above crude dimethyl fumarate was dissolved in methanol (11 L) at about 60° C. and the hot solution was filtered through 2 micron cartridge. The particle-free filtrate was concentrated and the obtained slurry mass was cooled to about room temperature and further to about 10° C. to about 15° C. and maintained at about the same temperature for about 1 h. The solid obtained was filtered, washed with methanol and dried at about 25° C. for about 6 h and further dried at about 40° C. to about 45° C. for about 12 h.
Yield: 510 g
Purity (HPLC): 99.85%
Chloride ion content: <100 ppm
Dimethyl sulfate content: below detection limit
Monomethyl fumarate content: <0.05%
Dimethyl maleate content: <3.1 ppm
PSD: Before milling-$D_{90}$: 672 μm, $D_{50}$: 242 μm, $D_{10}$: 72 μm
  After milling-$D_{90}$: 45 μm, $D_{50}$: 21 μm, $D_{10}$: 9 μm
XRPD peaks of dimethyl fumarate before milling:

| Pos. [°2Th.] | d-spacing [Å] | Rel. Int. [%] |
|---|---|---|
| 6.81 | 12.97 | 0.03 |
| 9.91 | 8.92 | 0.30 |
| 10.98 | 8.05 | 83.33 |
| 16.73 | 5.29 | 0.20 |
| 17.54 | 5.05 | 0.54 |
| 19.88 | 4.46 | 0.37 |
| 21.30 | 4.17 | 0.38 |
| 22.03 | 4.03 | 100.00 |
| 23.81 | 3.73 | 0.95 |
| 24.03 | 3.70 | 3.58 |
| 24.63 | 3.61 | 0.15 |
| 26.24 | 3.39 | 0.34 |
| 27.32 | 3.26 | 17.37 |
| 28.90 | 3.08 | 0.09 |
| 31.08 | 2.87 | 0.03 |
| 32.15 | 2.78 | 0.28 |
| 32.67 | 2.73 | 0.23 |
| 32.78 | 2.72 | 0.25 |
| 33.29 | 2.68 | 1.76 |
| 33.96 | 2.63 | 0.62 |
| 36.67 | 2.44 | 0.08 |
| 40.53 | 2.22 | 0.12 |
| 41.36 | 2.18 | 2.03 |
| 42.80 | 2.11 | 0.40 |
| 43.62 | 2.07 | 0.05 |
| 44.90 | 2.01 | 1.24 |
| 46.33 | 1.95 | 0.19 |
| 47.93 | 1.89 | 0.07 |

XRPD peaks of dimethyl fumarate after milling:

| Pos. [°2Th.] | d-spacing [Å] | Rel. Int. [%] |
|---|---|---|
| 10.95 | 8.07 | 59.02 |
| 16.75 | 5.29 | 10.22 |
| 17.52 | 5.06 | 25.19 |
| 19.75 | 4.49 | 0.16 |
| 22.00 | 4.03 | 66.62 |
| 22.31 | 3.98 | 3.30 |
| 24.04 | 3.70 | 100.00 |
| 26.24 | 3.39 | 15.20 |
| 27.35 | 3.25 | 95.19 |
| 28.88 | 3.09 | 2.80 |
| 31.08 | 2.87 | 0.21 |
| 32.15 | 2.78 | 0.98 |
| 32.83 | 2.72 | 4.91 |
| 33.24 | 2.69 | 1.69 |
| 33.90 | 2.64 | 8.56 |
| 34.70 | 2.58 | 2.76 |
| 35.37 | 2.53 | 0.29 |
| 36.64 | 2.45 | 0.98 |
| 37.23 | 2.41 | 0.25 |
| 38.93 | 2.31 | 1.08 |
| 39.53 | 2.27 | 0.42 |
| 40.14 | 2.24 | 1.12 |
| 40.49 | 2.22 | 1.23 |
| 41.33 | 2.18 | 8.91 |
| 42.98 | 2.10 | 5.58 |
| 44.86 | 2.01 | 0.72 |
| 45.56 | 1.98 | 0.46 |
| 46.48 | 1.95 | 2.82 |
| 46.96 | 1.93 | 0.95 |
| 47.94 | 1.89 | 1.49 |
| 48.65 | 1.87 | 1.29 |

Example 3 Preparation of Dimethyl Fumarate

To a suspension of fumaric acid (10 g) in toluene (80 mL) was added trimethyl orthoacetate (16.9 g) drop wise. The reaction mixture was refluxed for about 6 h. The reaction mixture was then cooled to about room temperature. Water (50 mL) added to the reaction mixture. The reaction mixture was stirred for about 30 min and the two layers were separated. The organic layer was washed with 5% aqueous sodium bicarbonate solution and then with water and concentrated under reduced pressure at about below 40° C. The obtained residue was slurred with methanol (30 mL) for about 30 min. The slurry mass was filtered, washed with methanol and dried at about 25° C. for about 6 h and further dried at about 40° C. to about 45° C. for about 12 h. Yield: 6.66 g Example 4 Preparation of Dimethyl Fumarate To a suspension of fumaric acid (10 g) in tert-butyl methyl ether (50 mL) was added perchloric acid (1.67 g) and the reaction mixture was refluxed for 18 h. The reaction mixture was then cooled to about room temperature and 20% sodium carbonate solution (100 mL) was added to it. The reaction mixture was stirred for about 30 min and methylene chloride (50 mL) was added to it. The reaction mixture was stirred for about 30 min and the two layers were separated. The aqueous layer was again extracted with methylene chloride (50 mL) and the combined organic layer was concentrated under reduced pressure at about below 35° C. The obtained residue was slurred with methanol (30 mL) for about 30 min. The slurry mass was filtered, washed with methanol and dried at about 25° C. for about 6 h and further dried at about 40° C. to about 45° C. for about 12 h. Yield: 9.3 g Example 5 Preparation of Dimethyl Fumarate To a suspension of fumaric acid (10 g) in methanol (65.22 mL) was added p-toluene sulfonic acid (14.83 g) in one lot at about 25° C. The reaction mixture was heated to about 67° C. to about 70° C. and was maintained at about the same temperature for about 5 h. The reaction mixture was then cooled to about 15° C. to about 20° C. and was maintained at about the same temperature for about 2 h. The solid obtained was filtered and washed with methanol and dried at about 25° C. for about 6 h and further dried at about 40° C. to about 45° C. for about 12 h. Yield: 10.3 g Example 6 Preparation of Dimethyl Fumarate To a suspension of fumaric acid (1 kg) in methanol (6 L) was added acetyl chloride (0.68 kg) at temperature in the range of 25-45° C. over a period of about 30 min. The reaction mixture was maintained at about 60° C.-70° C. for about 2.5 h. If required the above process was repeated and the reaction mass was heated at about 60° C.-70° C. for about 2.5 h. The reaction mixture was then cooled to about 15-20° C. and was maintained for about 1 h. The slurry obtained was centrifuged to obtain a wet solid. The wet solid obtained above was slurried with sodium bicarbonate and stirred at 25-30° C. for about 1 hour filtered and dried at about 25° C. for about 6 h and further dried at about 40° C. to about 45° C. for about 12 h.
Yield: 550 g The above crude dimethyl fumarate was dissolved in methanol and the hot solution was filtered through 2 micron cartridge. The particle-free filtrate was concentrated and the obtained slurry mass was cooled to about room temperature first and further to 10° C. to 15° C. and maintained for about 1 h. The solid obtained was filtered, washed with methanol and dried at about 25° C. for about 6 h and further dried at about 40° C. to about 45° C. for about 6 h.
Purity (HPLC): 99.9%
Chloride ion content: <100 ppm
Dimethyl sulfate content: below detection limit
Monomethyl fumarate content: <0.02%
Fumaric acid: Not detected (below 0.01%)
Dimethyl maleate content: <3.1 ppm
Monomethyl maleate: <3.1 ppm
XRPD peaks of dimethyl fumarate

| Pos. [°2Th.] | d-spacing [Å] | Rel. Int. [%] |
|---|---|---|
| 2.063 | 42.80 | 0.13 |
| 6.85 | 12.89 | 0.05 |
| 9.88 | 8.94 | 0.36 |
| 10.95 | 8.07 | 87.44 |
| 16.76 | 5.28 | 0.06 |
| 17.41 | 5.09 | 0.21 |
| 19.85 | 4.47 | 0.41 |
| 21.23 | 4.18 | 0.45 |
| 22.00 | 4.03 | 100.00 |
| 24.04 | 3.70 | 3.50 |
| 26.20 | 3.40 | 0.59 |
| 27.36 | 3.25 | 1.70 |
| 28.86 | 3.09 | 0.02 |
| 31.07 | 2.87 | 0.02 |
| 32.14 | 2.78 | 0.04 |
| 33.26 | 2.69 | 1.63 |
| 33.97 | 2.63 | 0.13 |
| 36.44 | 2.46 | 0.03 |
| 41.28 | 2.18 | 2.96 |
| 42.82 | 2.11 | 0.17 |
| 43.62 | 2.07 | 0.07 |
| 44.87 | 2.01 | 1.12 |
| 46.22 | 1.96 | 0.05 |
| 47.96 | 1.89 | 0.04 |
| 33.26 | 2.69 | 1.63 |
| 33.97 | 2.63 | 0.13 |
| 36.44 | 2.46 | 0.03 |
| 41.28 | 2.18 | 2.96 |
| 42.82 | 2.11 | 0.17 |
| 43.62 | 2.07 | 0.07 |
| 44.87 | 2.01 | 1.12 |
| 46.22 | 1.96 | 0.05 |

Ex 6a, 6b, 6c, 6d, 6e were carried out by the procedure disclosed in Example 6 to obtain dimethyl fumarate and the particle size distribution obtained was as below.

| Ex. No. | D(10) μm | D(50) μm | D(90) μm | D(4,3) μm |
|---|---|---|---|---|
| 6 | 47.3 | 181.9 | 427.2 | 213.8 |
| 6a | 39.7 | 168.8 | 412.6 | 201.9 |
| 6b | 55.1 | 204.6 | 466.5 | 236.9 |
| 6c | 53.6 | 199.1 | 465.2 | 234.0 |
| 6d | 74.2 | 234.8 | 503.0 | 265.4 |
| 6e | 97.5 | 270.9 | 546.0 | 299.6 |

The invention claimed is:
1. A process for the preparation of dimethyl fumarate, a compound of formula I,

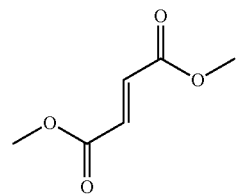

I in a purity of at least 99.0% as determined by HPLC, containing less than 400 ppm of an anion of a mineral acid and less than 5 ppm of dimethyl maleate and having a D90 particle size of at least 400 μm, the process comprising:

(a) reacting fumaric acid with an acyl halide in methanol to obtain dimethyl fumarate, a compound of formula I, wherein a molar equivalent of the acyl halide is in the range of from about an equimolar amount to about 2 times the molar amount with respect to fumaric acid;

(b) subjecting dimethyl fumarate, the compound of formula I, to treatment with a base; and (c) isolating dimethyl fumarate, the compound of formula I, from crystallization in a solvent, in a purity of at least 99.0% as determined by HPLC, containing less than 400 ppm of an anion of a mineral acid and less than 5 ppm of dimethyl maleate and having a D90 particle size of at least 400 μm.

2. The process of claim 1, wherein the anion of a mineral acid is selected from the group consisting of chloride, bromide, iodide, fluoride, sulphate, nitrate and phosphate.

3. The process of claim 1, wherein the isolated dimethyl fumarate, a compound of formula I, is free of dimethyl sulfate.

4. The process of claim 1, wherein the isolated dimethyl fumarate is free of dimethyl sulfate and has a monomethyl fumarate content of less than 0.15%.

5. The process of claim 1, wherein the solvent in step (c) is selected from the group consisting of an alcohol, an ester, a ketone, an ether, a haloalkane, acetonitrile; dimethyl sulfoxide; dimethyl formamide; dimethyl acetamide; water and mixtures thereof.

6. The process of claim 1, wherein the solvent in step (c) is methanol.

7. The process of claim 1, wherein the isolated dimethyl fumarate obtained in step (c) has a D90 particle size of 400 to 600 μm.

8. The process of claim 6, wherein the isolated dimethyl fumarate is characterized by XRPD peaks at 2-theta 10.9, 22.0, 24.0 and 27.3±0.2°.

* * * * *